United States Patent [19]
Ono et al.

[11] Patent Number: 5,970,425
[45] Date of Patent: *Oct. 19, 1999

[54] LIQUID CHROMATOGRAPH SYSTEM AND LIQUID CHROMATOGRAPH ANALYSIS METHOD

[75] Inventors: Takayuki Ono; Kiyotoshi Mori, both of Hitachinaka, Japan

[73] Assignee: Hitachi, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/828,485

[22] Filed: Mar. 31, 1997

[30] Foreign Application Priority Data

Apr. 8, 1996 [JP] Japan .................................. 8-084974

[51] Int. Cl.$^6$ .................................................. G01N 30/02
[52] U.S. Cl. .......................... 702/31; 702/183; 702/188
[58] Field of Search .................................. 364/496–499, 364/130–132, 138, 140–141, 184–186, 189, 528.01, 528.08; 73/61.52; 210/656, 659; 422/70; 436/161; 702/31, 182, 183–188

[56] References Cited

U.S. PATENT DOCUMENTS

| | | | |
|---|---|---|---|
| 4,399,502 | 8/1983 | MacDonald et al. | 364/189 |
| 4,468,331 | 8/1984 | Antle et al. | 210/659 |
| 4,674,323 | 6/1987 | Rulf et al. | 73/61.52 |
| 5,436,166 | 7/1995 | Ito et al. | 436/161 |
| 5,532,941 | 7/1996 | Lin | 702/186 |
| 5,594,663 | 1/1997 | Messaros et al. | 702/184 |
| 5,610,835 | 3/1997 | Dominguez et al. | 364/497 |

*Primary Examiner*—Melanie A. Kemper
*Attorney, Agent, or Firm*—Kenyon & Kenyon

[57] ABSTRACT

An analyzing method of a liquid chromatograph system which includes a plurality of chromatograph units each made up of a number of devices, obtains an analysis result by processing measurement data from chromatograph units using a data processor. System configurations are defined along with analysis parameters corresponding to the system configurations and stored in a main storage provided in the data processor. The stored analysis parameters are sent to chromatograph units as are requests to execute a measurement operations and, in the case of an error, requests to return peculiar information about each device. Each device of the chromatograph unit executes a measurement operation in response to a measurement operation request from the main controller and sends measurement data to the main controller for storage in the main storage in association with the analysis parameters. It also checks whether an error was produced in any of the devices during the measurement operation, and' upon detection of an error, sends the error information to the main controller, acquires the peculiar information about each device and sends the peculiar information to the main controller. The main controller creates an error analysis information file for analyzing the error on the basis of the error information, the peculiar information, and the analysis parameters, and stores the error analysis information file in the main storage in association with the system configuration. The information in this file may then be out put with an output device.

7 Claims, 7 Drawing Sheets

| | RETENTION TIME (min) | ± PERMISSIBLE WIDTH (min) |
|---|---|---|
| NE | 1.00 | 0.30 |
| E | 1.50 | 0.50 |
| DA | 2.50 | 1.00 |

ANALYSIS REPORT

USER NAME                                                                ANALYSIS DATE

DATA PROCESSOR SOFTWARE PART NO.

SYSTEM CONFIGURATION

PUMP A          : MODEL NAME ( SERIAL NO. )  REPLACEMENT DATE OF
                                             CONSUMING PART

AUTOSAMPLER: MODEL NAME ( SERIAL NO. )  REPLACEMENT DATE OF
                                        CONSUMING PARTS ,
                                        INJECTION CHECK RESULT

COLUMN          : MODEL NAME ( SERIAL NO. )  THE NUMBER OF INJECTION

COLUMN OVEN: MODEL NAME ( SERIAL NO. )  TEMPERATURE STABILITY

DETECTOR        : MODEL NAME ( SERIAL NO. )   Xe LAMP OPERATING TIME
                                              Xe LAMP ENERGY
                                              WL ERROR

UNIT SETUP PARAMETERS

PUMP A          PRESSURE LIMIT UPPER AND LOWER LIMITS
                PUMP TIME PROGRAM TABLE

AUTOSAMPLER     INJECTION PARAMETERS

OVEN            TEMPRATURE UPPER LIMIT
                SET TEMPERATURE

DETECTOR        DETECTOR TIME PROGRAM TABLE

GRAPH OF CHANGE IN PRESSURE AND TEMPERATURE WITH TIME

LIQUID CHROMATOGRAPH SYSTEM AND LIQUID CHROMATOGRAPH ANALYSIS METHOD

BACKGROUND OF THE INVENTION

The present invention relates to a liquid chromatograph having a plurality of chromatograph units for separating and analyzing a sample as a target to be analyzed by an eluant. More particularly, the invention relates to a liquid chromatograph having a configuration for analyzing an error that occurred in a device in a chromatograph unit.

The liquid chromatography is the technique of separating and analyzing a sample as a target to be analyzed by using eluant in a column for analysis which is retained at a constant temperature. A liquid chromatograph in which a system is constructed by including a plurality of chromatograph units for performing such analysis and which enables a number of samples to be analyzed is known. Presently, when an error in measurement occurs in such a liquid chromatograph system, an operator collects and writes information regarding the error together with the system configuration of the chromatograph units actually used for measurement, measurement and setup parameters of the devices in each chromatograph unit, and the data processing parameters of each chromatograph unit. The operator analyzes the location where the error occurred, the kind of error, the occurrence state of the error, and the like on the basis of the written information and adopts a means for avoiding the occurrence of the error on the basis of the analysis result.

In the liquid chromatograph system constructed of a plurality of chromatograph units, since the operations of the respective chromatograph units are complicatedly related, it is important to obtain accurate information in order to analyze the error.

However, the system configuration of each chromatograph unit, measurement and set parameters, data processing parameters, information regarding the error, and the like are collected and written manually by the operator directly from a parameter setup picture plane or the like. Therefore, there are cases when the information necessary for analyzing the error is omitted or the data is erroneously written, and proper means for avoiding the error cannot be obtained and time is wasted.

SUMMARY OF THE INVENTION

It is an object of the invention to provide a liquid chromatograph constructed of a plurality of chromatograph units, which can automatically obtain information for analyzing an error without omitting or erroneously writing necessary information and can obtain proper means for avoiding the error.

According to the invention, the above object is achieved by a liquid chromatograph system comprised of a plurality of chromatograph units each having: an autosampler for sampling a sample as an object to be analyzed and supplying it to a column for analysis; a pump for feeding eluant to the column; a column oven for maintaining the column at a constant temperature; and a detector for collecting measurement data in the column. The liquid chromatograph system is for processing the measurement data from the chromatograph units via a data processor, thereby obtaining a result to the analysis, wherein the system comprises: main storage means, which is provided in the data processor, for storing the configuration and analysis parameters of the devices in each of the chromatograph units; main control means, which is provided in the data processor, for sending the analysis parameters stored in the main storage means to each of the chromatograph units, and requesting the chromatograph units to execute a measurement operation and to return peculiar information about each device; and unit control means, which is provided in each of the chromatograph units, allowing each device in the chromatograph unit to execute the measurement operation under the analysis parameters for the measurement operation requested from the data processor, acquire the peculiar information about each device, check whether an error occurred in a device in the chromatograph unit, and send any error information and the peculiar information about each device to the main control means. Further, the main control means analyzes any error that occurred in a chromatograph unit on the basis of the error information, the peculiar information, and the analysis parameters and the main storage means stores the error analysis results in correspondence with the configuration of devices in each chromatograph unit.

The liquid chromatograph may also provide an error analysis result output means for outputting the error analysis results stored in the main storage means.

According to the invention as mentioned above, the configuration of devices in each chromatograph unit, such as an autosampler, a pump, a column oven, a detector, and the like is stored in the main storage means of the data processor. The analysis parameters for measurement in each chromatograph unit are also stored in the main storage means. With respect to the device construction and the analysis parameters to be stored, for example, an operator inputs the respective parameters.

The analysis parameters for measurement are sent from the main control means to each chromatograph unit and a measurement operation is requested. For the measurement operation request, in each chromatograph unit, the unit control means allows the devices to execute the measurement operation on the basis of the analysis parameters, and peculiar information of the devices at the time is acquired. Data measured at this time is sent to the data processor via the unit control means or other routes. The measurement data is processed and the analysis result is obtained. When an error occurs in a device in a chromatograph unit, the unit control means checks the error and the error information is transmitted to the main control means. The main control means requests each chromatograph unit to transmit peculiar information about each device. In response to this request, the peculiar information of each device is transferred from the unit control means. peculiar information can be for example, injection quantity by the autosampler at the time of measurement, data of pressure change of the pump, data of temperature change of the column oven, detection data by the detector, or the like.

The main control means analyzes the error that occurred in a chromatograph unit on the basis of the error information and the peculiar information sent from the unit control means and the analysis parameters stored in the main storing means. The result of the analysis of the error is stored by the main storage means in correspondence with the devices of each chromatograph unit.

In the case where the error analysis result output means is further provided, the error analysis result is outputted after the above operations.

As mentioned above, according to the invention, the actual structure of each device in each chromatograph unit and the analysis parameters for measurement in each chromatograph unit are preliminarily stored in the main storing means. When an error occurs in a device in a chromatograph unit, the error analysis results are respectively stored in correspondence with the configuration of the devices. Therefore, the configuration of the devices of each chromatograph unit and the analysis parameters thereof are accurately recognized and information such as what error occurred in which device in which chromatograph unit can be accurately and promptly obtained without manual work. Without the possibility of omission or erroneous writing of necessary information, the proper means for avoiding the error can be obtained to deal with the error.

DESCRIPTION OF THE PREFERRED EMBODIMENT

An embodiment of a liquid chromatograph according to the invention will be described with reference to FIGS. 1 to 7.

Figure 1:
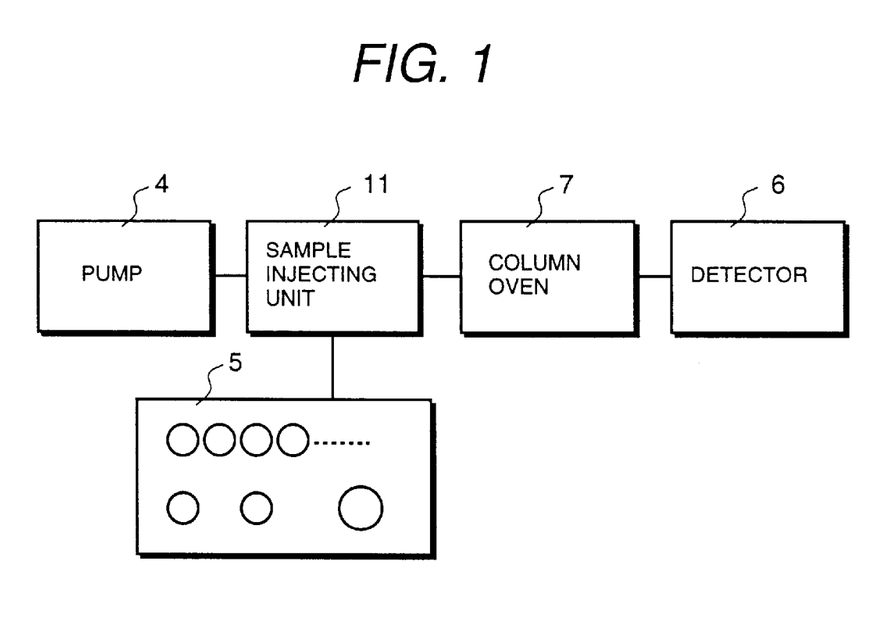
FIG. 1 is a diagram illustrating an overall system configuration of a liquid chromatograph according to an embodiment of the invention.

An overall configuration of a liquid chromatograph system will be described by FIG. 1. A mobile phase liquid is pumped by a pump 4. A sample is injected to the mobile phase liquid by an autosampler 5 and a sample injecting unit 11, thereby deriving a mixed liquid. The mixed liquid is supplied to a column 7 and is separated. Further, the mixed liquid passes through a column oven 7 and is detected by a detector 6.

Figure 2:
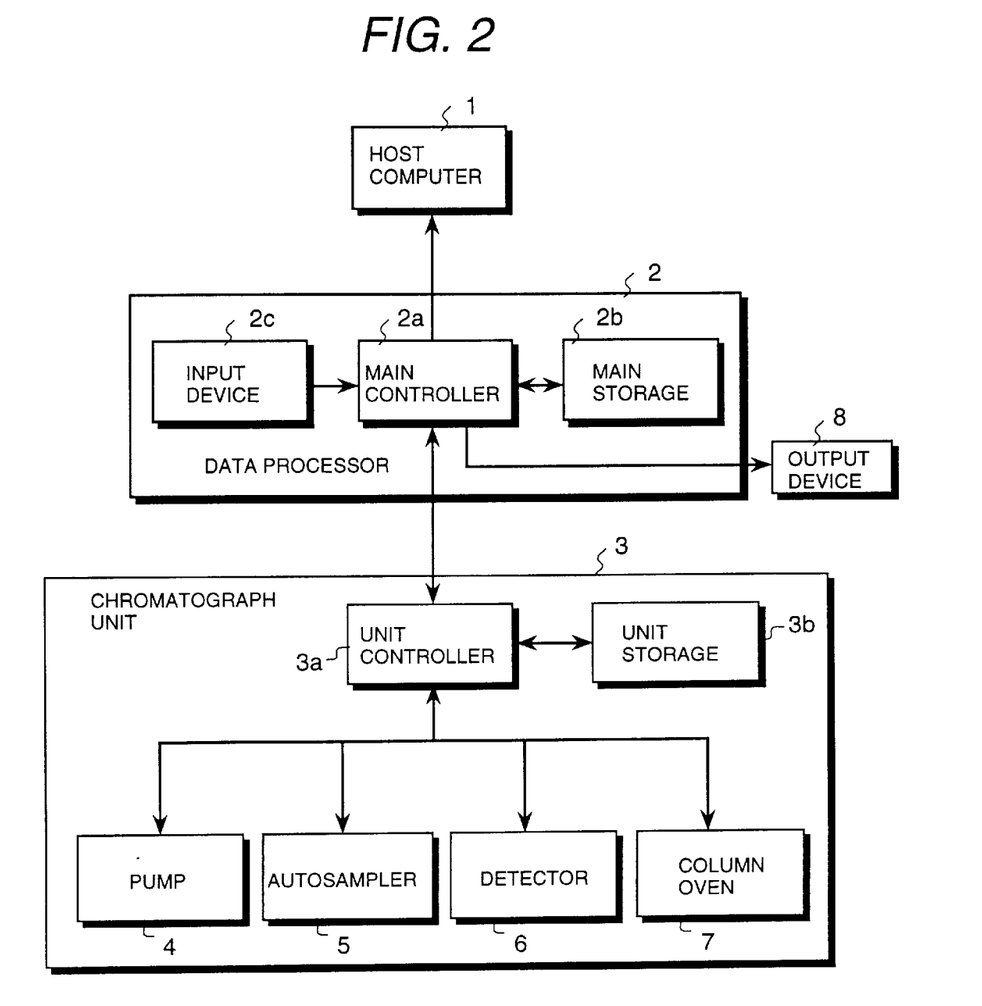
FIG. 2 is a diagram illustrating a control configuration of the liquid chromatograph.

A control system configuration will be described with reference to FIG. 2. A host computer 1 is a main computer for operating the whole system and managing data. A data processor 2 is connected to the host computer 1 via a communication line such as a public network, a private line, or the like. The data processor 2 has a main controller 2a, a main storage 2b, and an input device 2c. The main controller 2a in the data processor 2 is constructed by a circuit having various operational and control functions such as a measurement data waveform process, a quantitative calculation, and the like and is connected to a chromatograph unit 3 via the communication line. An output device 8 for properly outputting the contents stored in the main storage 2b is connected to the main controller 2a.

The chromatograph unit 3 has a unit controller 3a and a unit storage 3b. Devices such as the pump 4, autosampler 5, detector 6, column oven 7, and the like are connected to the unit controller 3a. The unit controller 3a is controlled by the main controller 2a and controls the devices and obtains information from the devices. Although not shown in the diagram, the system has a number of units similar to the chromatograph unit 3. Each of the chromatograph units 3 is connected to the main controller 2a in the data processor 2 via the communication line.

In the above, as the main storage 2b and the unit storage 3b, it is preferable to use a memory which is the same kind as that used in a general computer, such as SRAM, DRAM, or the like. An ordinary hard disk, a magnetooptic disk, or another disk apparatus can be also used.

Figure 3:
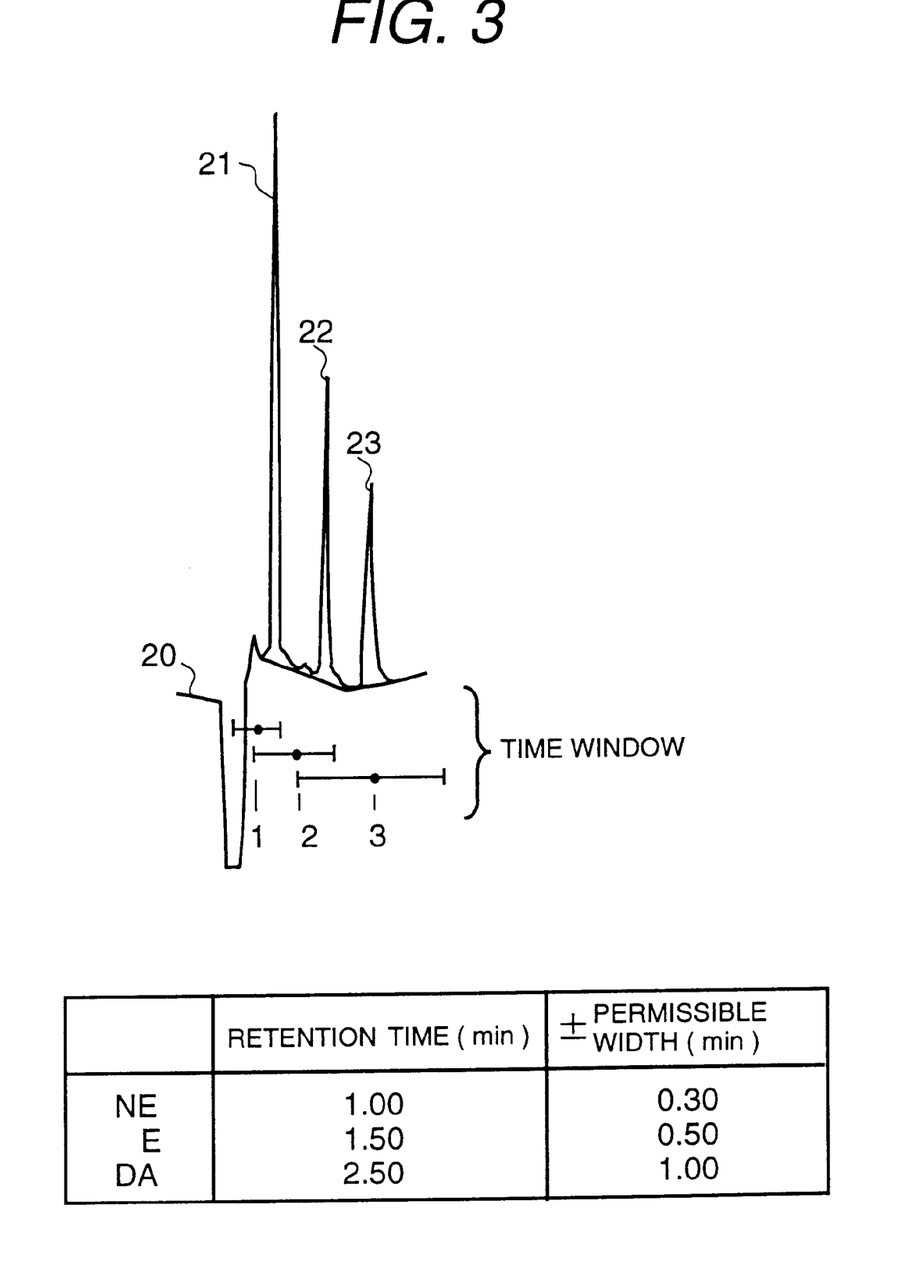
FIG. 3 is a diagram illustrating an example of a detection output of the liquid chromatograph.

An example of measurement is shown in FIG. 3. Peaks 21 to 23 are identified on the basis of the output chromatograph of the detector. For example, data between retention time 1 (corresponding to peak 21)+(−) and permissible time 1 is identified as a first substance (NE). Similarly, data between retention time 2 (corresponding to peak 22)+(−) and permissible time 2 is identified as a second substance (E), and data between retention time 3 (corresponding to peak 23)+(−) and permissible time 3 is identified as a third substance (DA).

Figure 4:
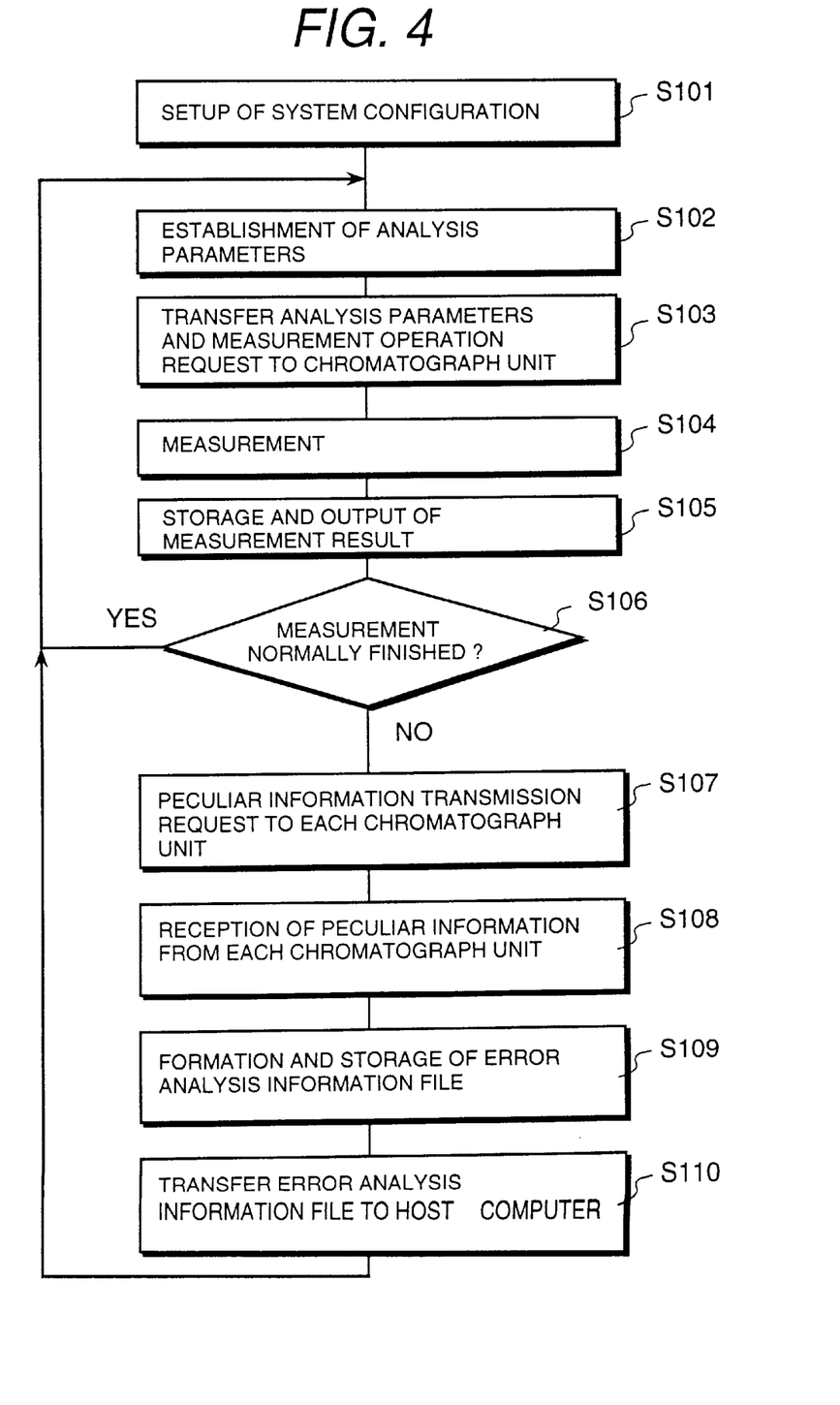
FIG. 4 is a flowchart showing a flow of a data process in a data processor shown in FIG. 2.
Figure 5:
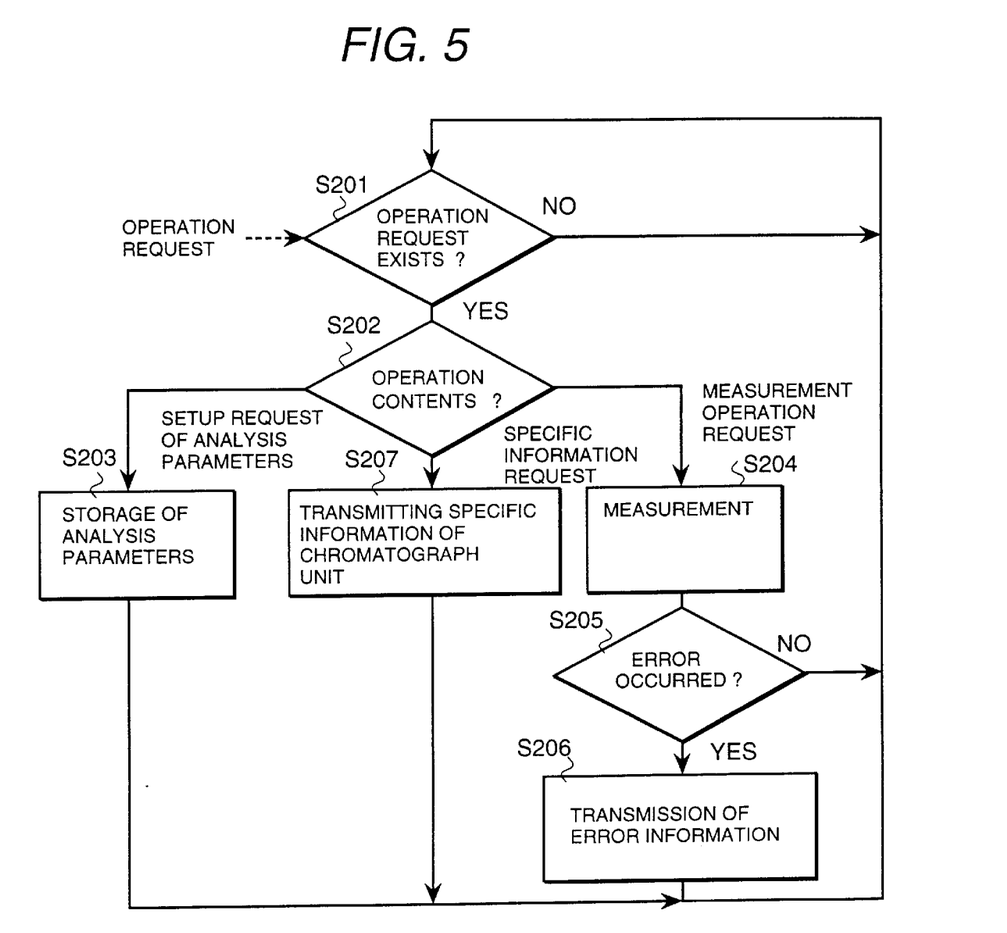
FIG. 5 is a flowchart showing a flow of an operation in a chromatograph unit shown in FIG. 2.

A flow of a process by the liquid chromatograph of the embodiment will be described with reference to FIGS. 4 to 7. FIG. 4 is a diagram showing a flow of a data process in the data processor 2. FIG. 5 is a diagram showing a flow of an operation in each chromatograph unit 3.

In step S101 in FIG. 4, a system configuration is set. That is, a system configuration file in which a configuration of devices in chromatograph units 3 to be used for measurement in the system, for example, the chromatograph units 3 to be used among a number of chromatograph units and devices (pump 4, detector 6, and the like) to be used in the chromatograph units are designated is formed and is stored into the main storage 2b.

In step S102, analysis parameters are established. That is, an analysis parameters file in which specific contents, e.g. what analysis is executed under which parameters, are designated is formed and is stored into the main storage 2b. The analysis parameters are, for example, an injection quantity and the number of injection times of the autosampler 5, the upper and lower limits of eluant mixing ratio, flow, and pressure by the pump 4, a temperature set value and the upper and lower limits of the temperature, measured wavelength and measurement time by the detector 6, and the like.

Figure 6:
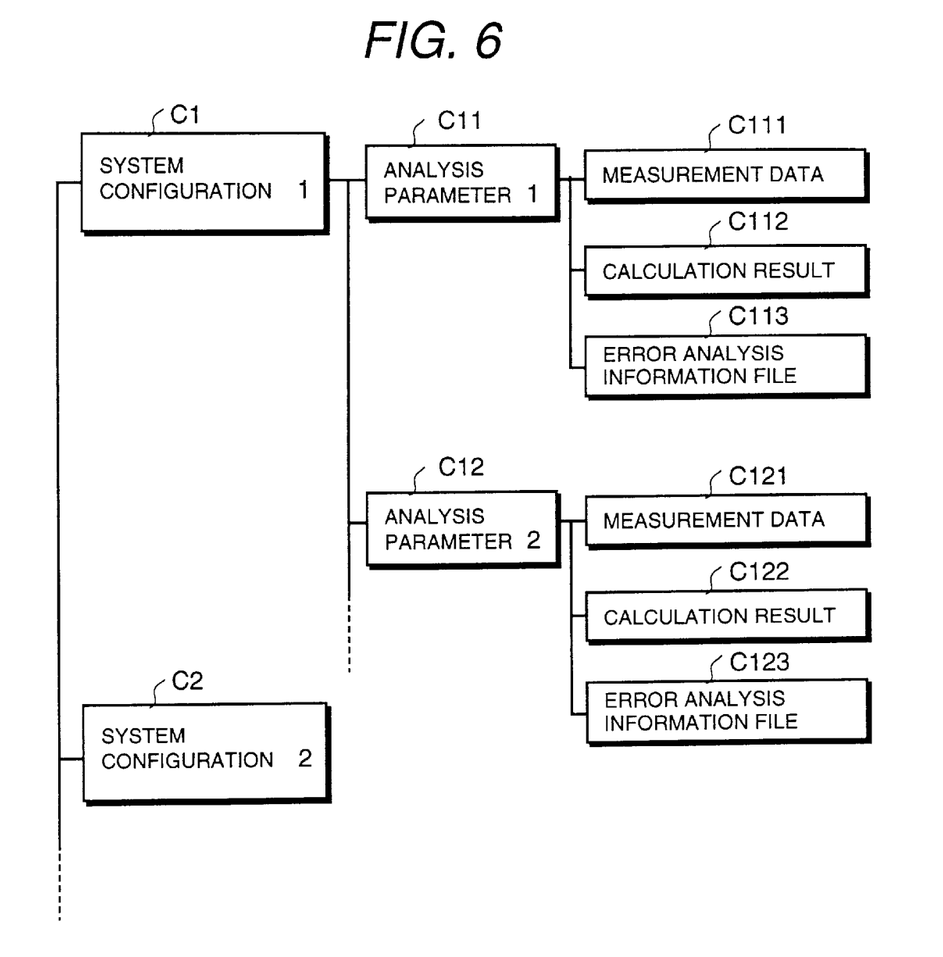
FIG. 6 is a diagram showing an example of a structure of a system configuration file to be stored in a main storage unit.

The processes in steps S101 and S102 are executed by the operator inputting operations by the input device 2c prior to the start of measurement. In the main storage 2b, for example as shown in FIG. 6, directories are formed under of system configuration files C1, C2, . . . , and analysis parameters files C11, C12, . . . are arranged in the relevant directories. The analysis parameter files in the same system configuration are stored in the same directory.

In step S103, a setup request of the analysis parameters and a measurement operation request formed in step S102 are transferred from the main controller 2a to the respective chromatograph units 3 via the communication lines.

The operation in each chromatograph unit 3 will be described below with reference to FIG. 5. In step S201, the unit controller 3a in each chromatograph unit 3 is waiting for the operation request from the main controller 2a. When any operation request is received via the communication line, the processing routine advances to step S202. In step S202, the chromatograph unit 3 discriminates the contents of the operation request received and the processing routine advances to a corresponding step.

When the operation request is the setup request of the analysis parameters, the routine advances to step S203. The unit controller 3a stores the analysis parameters received from the main controller 2a into the unit storage 3b. After that, the processing routine is again returned to step S201 and the system enters the operation request waiting state.

When the operation request is the measurement operation request, the processing routine is advanced to step S204 and the measurement operation is executed by the devices such as the pump 4, autosampler 5, detector 6, column oven 7, and the like according to the analysis parameters stored in the unit storage 3b under the control of the unit controller 3a. When the measurement operation in step S204 is finished, the unit controller 3a checks whether an error occurred during the measurement or not as shown in step S206. When there is no error, the processing routine is returned to step S201 and the unit controller 3a waits for the operation request. When an error occurred, as shown in step S206, the error information is transmitted to the main controller 2a of the data processor 2, the processing routine is returned to step S201, and the unit controller 3a waits for the operation request.

When the operation request received in step S201 is a peculiar information request (which will be described in step S107 in FIG. 4), the processing routine advances to step S207 and peculiar information of each of the devices such as the pump 4, autosampler 5, detector 6, column oven 7, and the like of the chromatograph unit 3 is collected and sent to the main controller 2a. The peculiar information of the devices can include, for example, with respect to the autosampler 5, information whether an accurate injection quantity was obtained or not with the set analysis parameters, and the number of use times (maintenance information) of replaceable parts such as an injection port, an injection valve, a syringe seal, and syringe pipe. With respect to the pump 4, there are data of pressure change (pressure profile) during the measurement indicating whether a proper pressure was obtained or not according to the set analysis parameters and the number of use times (maintenance information) of replaceable parts such as a pump seal. With respect to the column oven 7, data of temperature change (temperature profile) during the measurement indicating whether a proper temperature was retained or not according to the set analysis parameters. With respect to the detector 6, there is data indicative of a lamp energy value and wavelength indicating whether a detection was performed properly or not according to the set analysis parameters. After transmitting the peculiar information, the processing routine is returned to step S201 and the unit controller 3a enters the operation request waiting state.

Referring again to FIG. 4, a data process by the data processor 2 will be described. The setup request of the analysis parameters and the measurement operation request sent in step S103 are received and the chromatograph unit 3 is allowed to measure (step S104). The measurement data is received by the main controller 2a, and a necessary data process is executed while using the analysis parameters stored in the main storage 2b and the measurement results are stored into the main storage 2b together with the measurement data. The measurement results (measurement data and calculation results) are outputted to the output device 8 (step S105). In the main storage 2b, however, as shown in FIG. 6, the measurement data C111, C121, . . . , and calculation results C112, C122, . . . , are stored in the corresponding directories in the system configuration files C1, C2, . . . , every analysis parameters C11, C12, . . . . Subsequently, in step S106, the main controller 2a checks whether the measurement has been normally finished or not on the basis of the error information from each chromatograph unit 3. When no error occurred and the measurement has been normally finished, the processing routine is returned to step S102. When it is determined that the measurement was not finished normally due to occurrence of an error, the processing routine advances to step S107.

When an error occurred, that is, in step S107, the main controller 2a sends a peculiar information transmission request to the unit controller 3a of each chromatograph unit 3. As described in step S207 in FIG. 5, the main controller 2a receives the peculiar information of the devices sent from the unit controller 3a (step S108). The main controller 2a reads out the analysis parameters file for the chromatograph unit 3 formed in step S102 from the main storage 2b, performs a data process by using the analysis parameters and the peculiar information of the devices of the chromatograph unit 3, creates an error analysis information file, and stores the file to the main storage 2b (step S109). As shown in FIG. 6, each of error analysis information files C113, C123, . . . includes all information regarding the measurement such as a user name (operator name), analysis date and time, analysis parameters, and the like. The files C113, C123, . . . are stored in the directories under the system configuration files in correspondence with the system configurations C1, C2, . . . and the analysis parameters C11, C12, respectively. At this time point, the error analysis information files C113, C123, . . . can be outputted from the output device 8, for example, by being printed in a report format or the like.

After that, as shown in step S110, the main controller 2a issues a test command to the host computer 1 to confirm that it is connected to the host computer 1 on the network. When the confirmation of connection is returned from the host computer 1 in response to the test command, the main controller 2a transfers the error analysis information files stored in the main storage 2b to the host computer 1. The host computer 1 stores the transferred error analysis information file into an auxiliary storing device therein. A system manager on the host computer 1 side can consequently obtain means of avoiding errors on the basis of the transferred error analysis information file.

Figure 7:
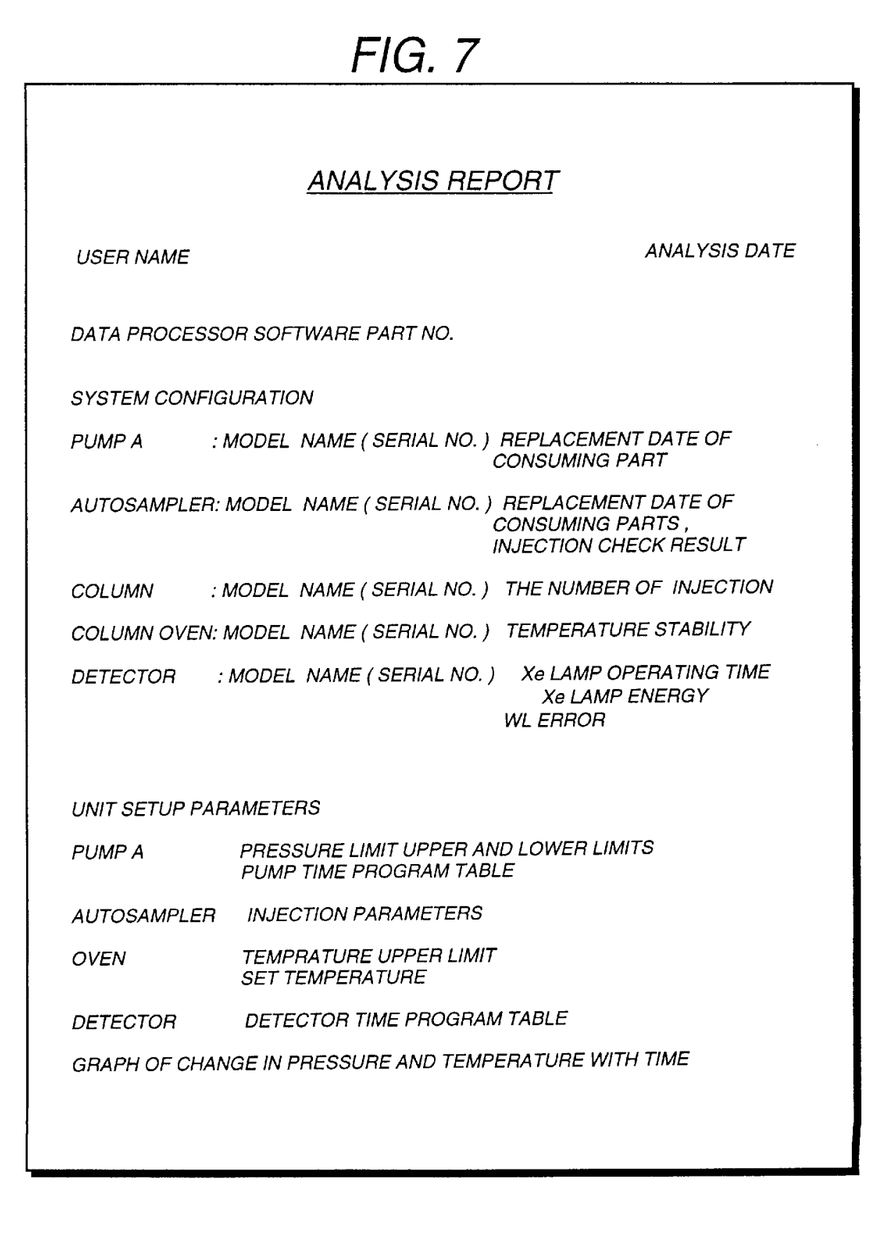
FIG. 7 is a diagram illustrating an example of an analysis report format of an error analysis information file.

FIG. 7 is a diagram showing an example of an analysis report format of the error analysis information file. The analysis report is outputted for every system configuration and has items for the user name, analysis date and time, a software part number showing the configuration of the data processor 2, system configuration of the devices, unit setup parameters of the devices, and the like. The unit setup parameters correspond to the analysis parameters.

According to the embodiment as mentioned above, the configuration of the devices such as the pump 4, autosampler 5, detector 6, column oven 7 and the like, that is, the devices of each chromatograph unit 3 have been preliminarily stored in the main storage 2b as a system configuration file. The analysis parameters of each device have been stored as an analysis parameter file in the main storage 2b. When an error occurs in the chromatograph unit 3, the error analysis information file is stored in correspondence with the system configurations file. Consequently, the configuration of the devices of each chromatograph unit 3 and the analysis parameters of each device are accurately recognized and information such as what error occurred in which device in which chromatograph unit can be accurately and promptly obtained, without manual work. Therefore, the proper error avoiding means, is obtained without the possibility of omission or erroneous writing of the necessary information and the error can be dealt with.

According to the invention, the configuration of each device of each chromatograph unit and the analysis parameters of each device have been stored in the main storage means. When an error occurs, the error analysis result is stored in correspondence with every configuration of the device. Thus, the error information can be accurately and promptly obtained without manual works. The proper error avoiding means can be obtained to deal with the error without the possibility of omission or erroneous writing of the necessary information.

We claim:

1. A liquid chromatograph system comprising:
    a plurality of chromatograph units each having an autosampler for sampling a sample as an object to be analyzed and supplying the sample to a column for analysis;
    a pump for supplying eluant to the column;
    a column oven for maintaining the column at a constant temperature;
    a detector for collecting measurement data produced in association with the supplying of the sample to the column; and
    a data processor for processing the measurement data from the chromatograph units, thereby obtaining an analysis result,
    wherein the system further comprises:
        a main storage, provided in the data processor, for storing system configurations in each of which a chromatograph unit to be used, of the plurality of chromatograph units, and devices in said chromatograph unit are defined along with analysis parameters corresponding to the system configurations;
        a main controller, provided in the data processor, for sending the analysis parameters stored in the main storage to the chromatograph unit defined in each system configuration, and requesting each device defined in each system to execute a measurement operation and, in the case of an error, to return peculiar information about each device defined in each system configuration; and
        a unit controller provided in each of the chromatograph units, for causing each device of the chromatograph unit to execute the measurement operation under the analysis parameters in response to a measurement operation request from the main controller and send measurement data to said main controller for storage in said main storage in association with said analysis parameters stored therein, check whether an error was produced in any of the devices defined in each system configuration during said measurement operation, and upon detection of an error, send the error information to said main controller, acquire the peculiar information about each device in response to a request from said main controller after an error has occurred and send the peculiar information about each device to the main controller; and
        the main controller creating an error analysis information file for analyzing said error on the basis of the error information, the peculiar information, and the analysis parameters, and storing said error analysis information file in the main storage in association with the system configuration in which the device in which said error occurred is defined.

2. The system according to claim 1, further comprising an error analysis information file output device for outputting the error analysis results from the error analysis information file stored in the main storage of the data processor.

3. An analyzing method of a liquid chromatograph system in which a plurality of chromatograph units are provided, each having an autosampler for sampling a sample as an object to be analyzed and supplying the sample to a column for analysis a pump for supplying eluant to the column, a column oven for maintaining the column at a constant temperature, a detector for collecting measurement data produced in association with the supplying of the sample to the column, and the column, the method obtains an analysis result by processing the measurement data from the chromatograph unit via a data processor,
    wherein the method comprises the steps of:
        storing system configurations in each of which a chromatograph unit to be used, of the plurality of chromatograph units, and devices in said chromatograph unit are defined along with analysis parameters corresponding to the system configurations in a main storage provided in the data processor;
        sending the analysis parameters stored in the main storage to the chromatograph unit defined in each system configuration and requesting each device defined in each system to execute a measurement operation and, in the case of an error, to return peculiar information about each device via a main controller which is provided in the data processor; and
        causing each device of the chromatograph unit to execute the measurement operation under the analysis parameters in response to a measurement operation request from the main controller and send measurement data to said main controller for storage in said main storage in association with said analysis parameters stored therein, check whether an error was produced in any of the devices defined in each system configuration during said measurement operation, and upon detection of an error, send the error information to said controller, acquire the peculiar information about each device in response to a request from said main controller after an error has occurred and send the peculiar information about each device to the main controller; and
        creating an error analysis information file for analyzing said error on the basis of the error information, the peculiar information, and the analysis parameters, and storing said error analysis information file in the main storage in association with the system configuration in which the device in which said error occurred is defined.

4. The method according to claim 3, wherein the error analysis result stored in the main storage of the data processor is outputted.

5. The method according to claim 4, wherein a pump replacement time is outputted.

6. The method according to claim 4, wherein a column replacement time is outputted.

7. The method according to claim 4, wherein the analysis result is outputted at the time of the analysis.

* * * * *